United States Patent [19]

Ayotte et al.

[11] Patent Number: 4,767,888
[45] Date of Patent: Aug. 30, 1988

[54] PRODUCTION OF COLE CROPS WHICH EXHIBIT TRIAZINE TOLERANCE

[75] Inventors: Renald R. Ayotte; Patricia M. Harney; Vincent S. Machado, all of Guelph, Canada

[73] Assignee: University of Guelph, Guelph, Canada

[21] Appl. No.: 17,595

[22] Filed: Feb. 24, 1987

[51] Int. Cl.[4] .......................... A01H 1/02; A01H 5/00
[52] U.S. Cl. .......................................... 800/1; 47/58; 47/DIG. 1
[58] Field of Search ...................... 47/1, 58, DIG. 1; 800/1

[56] References Cited

U.S. PATENT DOCUMENTS

| 4,517,763 | 5/1985 | Beversdorf et al. | 47/58 |
| 4,658,085 | 4/1987 | Beversdorf et al. | 47/58 |

OTHER PUBLICATIONS

Anderson, W. P. (from) *Weed Science Principles* (Second Edition) 1983 West Publishing Co. pp. 102–107, 248–253, 575–587 and 601–604 cited.

Stewart, J. M. "In Vitro Fertilization and Embryo Rescue", *Propagation of Higher Plants Through Tissue Culture; Emerging Technologies and Strategies* (Special Issue of) Environmental and Experimental Botany, Fergamon Press, 1981 pp. 301–315.

W. D. Beversdorf, J. Weiss-Lerman, L. R. Erickson and V. Souza Machado, "Transfer of Cytoplasmically-Inherited Triazine Resistance From Bird's Rape to Cultivated Oilseed Rape (*Brassica campestris* and *B. napus*)", Canadian Journal of Genetics and Cytology, 22, pp. 167–172, Jun. 1980.

V. Souza Machado, J. D. Bandeen, G. R. Stephenson and P. Lavigne, "Uniparental Inheritance of Chloroplast Atrazine Tolerance in *Brassica campestris*", Can. J. Plant Sci. 58: 977–981, 1978.

U. N., 1935. Genome-analysis in Brassica with special reference to the experimental formation of *B. napus* and peculiar mode of fertilization. Jap. J. Bot. 7: 389–452.

Calder R. A., 1937. Interpollination of Brassicas. New Zeal. J. of Agric. 55: 299–308.

Yarnell, S. H. 1956. Cytogenetics of the Vegetable Crops. II. Crucifers. Bot. Rev. 22: 81–166.

Honma, S. and W. L. Summers, 1976. Interspecific Hybridization between *Brassica napus* L. (Napobrassica group) and *B. oleracea* L. (Botrytis group). J. Amer. Soc. Hort. Sci. 101: 299–302.

Chiang, M. S., B. Y. Chiang and W. F. Grant, 1977. Transfer of Resistance to race 2 of *Plasmodiophora brassicae* from *Brassica napus* to cabbage (*B. oleracea* var. capitata. Euphytica 26: 319–326.

McNaughton, I. H. and C. L. Ross, 1978. Inter-specific and inter-generic Hybridization in the Brassicae with Special Imphasis on the Improvement of the Scot. Plant Breed. Sta. 1978: 75–110.

Olsson, G. and S. Ellerström, Polyploidy Breeding in Europe. In Tsunoda, S., K. Hinata and C. Gómez-Campo (eds.). Brassica Crops and Wild Allies. Japan Scientific Societies Press, Tokyo. (1980).

R. Ayotte, P. M. Harney and V. Souza-Machado, "The Production of Atrazine-Resistant *Brassica napus* x *B. oleracea* Hybrids", Cruciferae Newsletter 10, 87 (Nov. 1985).

M. Monnier, "Croissance et développment des embryons globularies de *Capsella bursa-pastoris* cultivés in vitro dans un milieu á base d'une nouvelle solution minérale", Soc. Bot. Fr., Memoires 1973, Coll. Morphologie: 179–194.

*Primary Examiner*—James R. Feyrer
*Attorney, Agent, or Firm*—Burns, Doane, Swecker & Mathis

[57] ABSTRACT

Improved plants of *Brassica oleracea* and seeds capable of forming the same are provided. Such plants are fully male and female fertile and possess the usual complement of 18 chromosomes. However, unlike previously available cole crops, these plants exhibit cytoplasmic triazine tolerance when atrazine is applied as a foliar spray at a rate of 1.5 kilograms per hectare. For the first time a triazine herbicide can effectively be used to destroy unwanted broadleaf weeds which have a propensity to grow in the same planting area with the cole crop. Accordingly, an improved process for producing a cole crop is provided through the application of triazine to the planting area.

36 Claims, No Drawings

PRODUCTION OF COLE CROPS WHICH EXHIBIT TRIAZINE TOLERANCE

BACKGROUND OF THE INVENTION

Cole crops (*Brassica oleracea* plants) are widely grown in many parts of the world. Such crops include cabbage (subspecies *capitata*), Savoy cabbage (subspecies *sabauda*), cauliflower (subspecies *botrytis*), broccoli (subspecies *italica*), curly kale (subspecies *fimbriata*), collard (subspecies *acephala*), kohl-rabi (subspecies *gonoyloides*), Brussels sprouts (subspecies *gemmifera*), Chinese kale (subspecies *alboglabra*), etc. The grower of the cole crop commonly purchases seed to produce the same or small immature plants which are transplanted.

The presence of weeds in the same planting area with the cole crop often has added significantly to the cost of production. For instance, hand-hoeing or mechanized cultivation frequently has been required to minimize competition from unwanted broadleaf weeds and grasses. Such a weed problem has been the most acute if the grower attempts to produce the cole crop from seeds as opposed to the growing of transplanted small plants. Unchecked weeds can lessen the ultimate cole crop yield, and in some instances will reduce the quality of the product through unavoidable contamination.

Heretofore the use of herbicides to control weeds growing among cole crops has met with only limited success. For instance, the use of compounds such as trifluralin and chlorthaldimethyl do not begin to adequately control the weed problem which commonly is encountered. Presently, weeds such as hairy gallinsoga, black nightshade and the wild mustards are costing cole crop producers large sums in hand-hoeing costs. Also, the commercial development of new herbicides is proving to be extremely expensive in view of the long testing and clearance requirements commonly imposed by governmental agencies. Such expense commonly cannot be justified for low-acreage crops including the cole crops. Also, some chemical herbicides formerly available for weed control in cole crops have been removed from the market, further exasperating the situation.

Heretofore cole crops (i.e., *Brassica oleracea*) have exhibited an absence of tolerance to triazine herbicides which has heretofore precluded the usage of such herbicides in an attempt to oontrol weeds which regularly appear in the planting area. Also, since triazines commonly are used as a herbicide with corn, residual amounts of the same in the soil commonly have had an adverse impact on a subsequently grown cole crop when one carries out crop rotation.

Cytoplasmically inherited triazine resistance previously has been available in *Brassica campestris* and *B. napus*. See in this regard, "Transfer of Cytoplasmically-Inherited Triazine Resistance From Bird's Rape to Cultivated Oilseed Rape (*Brassica campestris* and *B. napus*)", by W. D. Beversdorf, J. Weiss-Lerman, L. R. Erickson and V. Souza Machado appearing in the Canadian Journal of Genetics and Cytology, 22, Pages 167–172, June 1980. See also, "Uniparental Inheritance of Chloroplast Atrazine Tolerance in Brassica Campestris" by V. Souza Machado, J. D. Bandeen, G. R. Stephenson and P. Lavigne, Can. J. Plant Sci. 58:977–981, 1978. See also, U.S. Pat. No. 4,517,763 and copending U.S. patent application Ser. No. 797,916, filed Nov. 14, 1985 (now U.S. Pat. No. 4,658,085), which describe such herbicide tolerance in rape (i.e., *Brassic napus*) when combined with cytoplasmic male sterility, and the use of plants which possess such tolerance in improved hybridization processes. The desirability of also transferring such triazine tolerance to *Brassica oleracea* cole crops has heretofore been recognized by plant scientists to be a worthy objective and to possibly be within the realm of theoretical possibility if a way could be found to overcome significant problems inherent in this breeding approach.

The barriers to this interspecific hybridization heretofore have been regarded to be varied and complex. For instance, interspecific crosses of *Brassica oleracea* with *B. campestris* or *B. napus* previously have been recognized by plant scientists to be at best extremely difficult to achieve. Commonly the embryo resulting from the cross will abort. In those rare instances when the cross-pollination has produced an offspring, there has been no assurance that the offspring will be fertile and that it will be possible to backcross it to the recurrent parent (i.e., *Brassica oleracea*) and return to the normal 18 chromosome complement of *Brassica oleracea*. *Brassica campestris* has 20 chromosomes and *Brassica napus* has 38 chromosomes. See, for instance, the following technical articles:

U, N., 1935. Genome-analysis in Brassica with special reference to the experimental formation of *B. napus* and peculiar mode of fertilization. Jap. J. Bot. 7: 389–452.

Calder, R. A., 1937. Interpollination of Brassicas. New Zeal. J. of Agric. 55: 299–308.

Yarnell, S. H., 1956. Cytogenetics of the vegetable crops. II. Crucifers. Bot. Rev. 22: 81–166.

Honma, S. and W. L. Summers, 1976. Interspecific hybridization between *Brassica napus* L. (Napobrassica group) and *B. oleracea* L. (Botrytis group). J. Amer. Soc. Hort. Sci. 101: 299–302.

Chiang, M. S., B. Y. Chiang and W. F. Grant, 1977. Transfer of resistance to race 2 of *Plasmodiophora brassicae* from *Brassica napus* to cabbage (*B. oleracea* var. *capitata*). I. Interspecific hybridization between *B. napus* and *B. oleracea* var. *capitata*. Euphytica 26: 319–336.

McNaughton, I. H. and C. L. Ross, 1978. Interspecific and inter-generic hybridization in the Brassicae with special emphasis on the improvement of forage crops. Ann. Rep. of the Scot. Plant Breed. Sta. 1978: 75–110.

The transfer of resistance to race 2 of *Plasmodiophora brassicae* from *Brassica napus* to *B. oleracea* by Chiang et al. described in the above and subsequent articles is the only known published account of a gene transfer between the species. Accordingly, it has not heretofore been apparent to those skilled in plant technology how one could with certainty transfer triazine tolerance from *Brassica campestris* or *B. napus* to *B. oleracea* to achieve fully fertile plants having the 18 chromosomes characteristic of *B. oleracea*.

The technique of in vitro culture to rescue inviable interspecific hybrids has been used as early as 1925 to rescue hybrids of *Linum perenne* and *L. austriacum* as reported in Laibach, F., "Das Taubwerden von Bastardsamen und die Fünstliche Aufzucht früh absterbender Bastardembryonem", Z. Bot. 17: 417–459 (1925). This technique subsequently has been used to generate both interspecific and intergeneric hybrids in a large number of genera including Solanum, Lycopersicon, Oryza, Phaseolus, Brassica, Medicago, and Hordeum as reported in the following technical articles:

Jorgensen, C. A., 1928. The experimental formation of heteroploid plants in the genus Solanum. J. Genet. 19: 133–211.

Smith, P. G., 1944. Embryo culture of a tomato species hybrid. Proc. Amer. Soc. Hort. Sci. 44: 413–416.

Niles, J. J., 1951. Hybridization methods with paddy. Trop. Agric. Ceylon 107: 25–29.

Honma, S., 1955. A technique for artificial culturing of bean embryos. Proc. Amer. Soc. Hort. Sci. 65: 405–408.

Nishi, S., J. Kawata and M. Toda, 1959. On the breeding of interspecific hybrids between two genomes, "c" and "a", of Brassica through the application of embryo culture techniques. Jap. J. Breed. 8: 215–222.

Harberd, D. J., 1969. A simple effective embryo culture technique for Brassica. Euphytica 18: 425–429.

Fridriksson, S. and J. L. Bolton, 1963. Preliminary report on the culture of alfalfa embryos. Can. J. Bot. 41: 439–440.

Kasha, K. J. and K. N. Kao, 1970. High frequency haploid production in barley (*Hordeum vulgare* L.). Nature 225: 874–876.

Embryo culture also has been employed to re-synthesize *Brassica napus* from its two progenitor species *B. campestris* an *B. oleracea* as reported by Olsson, G. and S. Ellerstrm, öPolyploidy breeding in Europe. In Tsunoda, S., K. Hinata and C. Gómez-Campo (eds.). Brassica Crops and Wild Allies. Japan Scientific Societies Press, Tokyo. (1980).

Our early research efforts via embryo rescue and regeneration to accomplish the transfer of triazine tolerance without loss of fertility to *Brassica oleracea* are briefly reported in "The Production of Atrazine-Resistant *Brassica napus* x *B. oleracea* Hybrids," Cruciferae Newsletter 10, 87 (November, 1985). No 18 chromosome *Brassica oleracea* plant was produced during our early research or reported in such article.

It is an object of the present invention to provide an improved process for producing a *Brassica oleracea* cole crop in the substantial absence of unwanted weeds.

It is an object of the present invention to provide *Brassica oleracea* seeds which yield fully male and female fertile plants which exhibit cytoplasmic triazine tolerance.

It is an object of the present invention to provide fully male and female fertile *Brassica oleracea* plants which exhibit triazine tolerance.

It is an object of the present invention to provide an improved process for producing a cole crop wherein the necessity for hand and/or mechanized weed removal is substantially minimized.

It is an object of the present invention to take possible the successful growing of a cole crop in rotation with a corn crop wherein a triazine herbicide was applied to control weeds.

It is another object of the present invention to make possible the successful growing of a cole crop from seeds in the substantial absence of unwanted weeds without the need for substantial hand and/or mechanized weed removal.

It is a further object of the present invention to make possible the successful production of cole crop seeds substantially uncontaminated with other triazine susceptible weed seeds of the Brassicaceae or other plant families without the need for substantial hand and/or mechanized weed removal.

These and other objects, as well as the scope, nature, and utilization of the claimed invention, will be apparent to those skilled in the art from the following detailed description and appended claims.

SUMMARY OF THE INVENTION

It has been found that an improved process for producing a cole crop in the substantial absence of unwanted broadleaf weeds while growing in a planting area which normally would have the propensity to form such broadleaf weeds comprises:

(a) growing *Brassica oleracea* plants in the planting area which are fully male and female fertile, possess 18 chromosomes, and exhibit cytoplasmic triazine tolerance, (b) contacting the planting area with triazine in an amount sufficient to substantially destroy broadleaf weeds while maintaining said *Brassica oleracea* plants substantially intact, and (c) harvesting the cole crop.

*Brassica oleracea* seeds are provided which upon growth yield male and female fertile plants possessing 18 chromosomes which exhibit cytoplasmic triazine tolerance when atrazine is applied as a foliar spray at a rate of 1.5 kilograms per hectare.

*Brassica oleracea* plants are provided which are fully male and female fertile, possess 18 chromosomes, and exhibit cytoplasmic triazine tolerance when atrazine is applied as a foliar spray at a rate of 1.5 kilograms per hectare.

DESCRIPTION OF PREFERRED EMBODIMENTS

The process of the present invention is made possible through the development of novel fully fertile *Brassica oleracea* plants having the usual 18 chromosome complement which are capable of well withstanding the application of triazine herbicide. Heretofore, it has not been possible to apply a triazine herbicide to *Brassica oleracea* plants in a concentration sufficient to kill broadleaf weeds without also severely harming the cole crop.

Representative cole plants which can be rendered tolerant to triazine are cabbage (*B. oleracea* subspecies *capitata*), Savoy cabbage (*B. oleracea* subspecies *sabauda*), cauliflower (*B. oleracea* subspecies *botrytis*), broccoli (*B. oleracea* subspecies *italica*), curly kale (*B. oleracea* subspecies *fimbriata*), collard (*B. oleracea* subspecies *acephala*), kohl-rabi (*B. oleracea* subspecies *gongyloides*), Brussels sprouts (*B. oleracea* subspecies *gemmifera*), Chinese kale (*B. oleracea* subspecies *alboglabra*), etc.

We have found that *Brassica napus* rape plants developed at University of Guelph, Guelph, Ontario, Canada, and elsewhere which possess the usual 38 chromosomes characteristic of the species can serve as the source for the triazine tolerance which is imparted to the *B. oleracea* plants. Triazine resistance was first discovered in *B. campestris* as reported by B. Maltais and C. J. Bouchard in "Une moutarde des oiseaux (*Brassica rapa* L.) résistante á l'atrazine", Phytoprotection 59: 117–119 (1978). It subsequently was transferred to *B. napus* as reported by W. D. Beversdorf, J. Weiss-Lerman, L. R. Erickson and V. Souza Machado in "Transfer of Cytoplasmically-Inherited Triazine Resistance From Bird's Rape to Cultivated Oilseed Rape (*Brassica campestris* and *B. napus*)", Can. J. Genet. Cytol. 22: 167–172 (1980). Such triazine tolerance is recognized to be a cytoplasmically-determined trait as reported by V. Souza Machado, J. D. Bandeen, G. R. Stephenson and P. Lavigne, "Uniparental Inheritance of Chloroplast Atrazine Tolerance in *Brassica campestris*", Can. J. Plant Sci. 58: 977-981 (1978), and is conditioned by a single nucleotide change in a chloroplast gene as reported by J. Hirschberg, A. Bleecker, D. J. Kyle, L. McIntosh, and C. J. Arntzen in "The Molecular Basis of Triazine-Herbicide Resistance in Higher Plant Chloroplasts", Z. Naturforsch 39C: 412-421 (1984). Rape seeds (i.e., canola seeds) capable of forming the *Brassica napus* plants which possess triazine tolerance are available to plant breeders from the Chairman, Department of Crop Science, University of Guelph, Ontario, Canada N1G 2WI, under the designation 'ATR-5TW,' Catalogue No. 83-016 in its 1986 Germ Plasm Releases. Also, triazine tolerant *Brassica napus* seeds from this program have been deposited in the National Seed Storage Laboratory at Fort Collins, Colorado, USA, under Sample No. ATR-5TW, Laboratory Accession No. BNa-21, and Serial No. 180,171. Seeds of the triazine tolerant spring canola 'OAC Triton' are available from Beers Seeds Ltd., R.R.4, Arthur, Ontario, Canada NOG IAO, and likewise can well serve as a suitable triazine tolerant *Brassica napus* source. Also, seeds of the triazine tolerant rutabaga (*Brassica napus* subspecies *rapifera*) cultivar 'Laurentian' are available from Dr. Vincent Souza Machado, Department of Horticultural Science, University of Guelph, Ontario, Canada N1G 2WI.

Our research has found that the required *Brassica oleracea* plants can be developed by an interspecific introgressive backcrossing protocol. *B. napus* plants possessing triazine tolerance are used as the maternal parent and *B. oleracea* plants are used as the recurrent parent in a procedure which combines in vitro embryo culture (as described) and plant regeneration (as described).

A *Brassica napus* plant which exhibits cytoplasmic triazine tolerance is hand-emasculated and is pollinated in the bud stage with pollen from a *B. oleracea* which lacks triazine tolerance. The parent plants used in this cross are grown in a growth room illuminated with Sylvania metal arc lamps ($215 \mu mol\ m^{-2} s^{-1}$ at canopy level) for 16 hours per day. The temperature in growth room is maintained at approximately 20° C. during the day and at approximately 16° C. during the night. Siliques are removed from the *Brassica napus* seed parent approximately 12 to 17 days following the pollination. These are surface sterilized in a laminar flow hood for 20 minutes in a 50 percent aqueous solution of household bleach (5% sodium hypochlorite), and are rinsed for 30 minutes with sterilized distilled water. Intact ovules are obtained from the siliques and are placed on the bottom of a 20×60 mm. plastic petri dish and are carefully split lengthwise in half while under a dissecting microscope using needle forceps.

Next 5 ml. of liquid embryo culture medium as described by M. Monnier in "Croissance et développment des embryons globulaires de *Capsella bursa-pastoris* cultivés in vitro dans un milieu á base d'une nouvelle solution minérale", Soc, Bot. Fr., Mémoires 1973, Coll. Morphologie: 179:194, are poured into the petri dish.

The in vitro embryo culture medium contains the following in water expressed in grams per liter:

| | | | |
|---|---|---|---|
| $KNO_3$ | 1.9 | $H_3BO_3$ | 0.0124 |
| $CaCl_2.2H_2O$ | 0.88 | $MnSO_4.H_2O$ | 0.0336 |

-continued

| | | | |
|---|---|---|---|
| $NH_4NO_3$ | 0.825 | $ZnSO_4.7H_2O$ | 0.021 |
| KCl | 0.350 | KI | 0.00166 |
| $MgSO_4.7H_2O$ | 0.370 | $Na_2MoO_4.2H_2O$ | 0.0005 |
| $KH_2PO_4$ | 0.170 | $CuSO_4.5H_2O$ | 0.00005 |
| $FeSO_4.7H_2O$ | 0.0111 | $CoCl_2.6H_2O$ | 0.00005 |
| $Na_2EDTA$ | 0.0149 | thiamine | 0.0001 |
| piridoxine | 0.0001 | glutamine | 0.400 |
| sucrose | 120.0 | agar | 7.0 |

The pH of the liquid embryo culture medium is adjusted to 5.8 with NaOH prior to the addition of agar and autoclaving.

The petri dish containing the plant material and the in vitro embryo culture medium next is sealed with parafilm and is placed in a rotary shaker operating at 60 rpm while present in a growth room illuminated with Sylvania cool white 40 watt fluorescent bulbs ($40 \mu mol\ m^{-2} s^{-1}$) for 16 hours per day. The temperature in the growth room is maintained at approximately 25° C.

After approximately 14 to 21 days the surviving interspecific embryos are transferred from the in vitro embryo culture medium to three different regeneration media as described by W. A. Keller in "Anther Culture of Brassica," Cell Culture and Somatic Cell Genetics of Plants 1: 201-310 (1984).

Initially rescued embryos are placed for approximately two weeks on a first regeneration medium which contains the following in water expressed in grams per liter:

| | | | |
|---|---|---|---|
| $KNO_3$ | 2.5 | $H_3BO_3$ | 0.003 |
| $CaCl_2.2H_2O$ | 0.150 | $MnSO_4.H_2O$ | 0.010 |
| $MgSO_4.7H_2O$ | 0.250 | $ZnSO_4.7H_2O$ | 0.002 |
| $(NH_4)_2SO_4$ | 0.134 | KI | 0.00075 |
| $NaH_2PO_4.H_2O$ | 0.150 | $Na_2MoO_4.2H_2O$ | 0.00025 |
| Sequestrene 330-Fe | 0.040 | $CuSO_4.5H_2O$ | 0.000025 |
| inositol | 0.100 | $CoCl_2.6H_2O$ | 0.000025 |
| piridoxine | 0.001 | sucrose | 30.0 |
| nicotinic acid | 0.001 | agar | 8.0 |
| thiamine | 0.010 | | |

The pH of the first regeneration medium is adjusted to 5.8 with NaOH prior to the addition of agar and autoclaving.

Next, the embryos are placed for approximately two weeks on a second regeneration medium to form normal shoots which usually originate on the hypocotyl of the embryo. If shoots are not produced after two weeks, the embryos should be trimmed of dead tissue and again transferred to a fresh second regeneration medium. The second regeneration medium contains the following in water expressed in grams per liter;

| | | | |
|---|---|---|---|
| $KNO_3$ | 1.900 | $H_3BO_3$ | 0.0062 |
| $NH_4NO_3$ | 1.650 | $MnSO_4.4H_2O$ | 0.0223 |
| $CaCl_2.2H_2O$ | 0.440 | $ZnSO_4.7H_2O$ | 0.0086 |
| $MgSO_4.7H_2O$ | 0.370 | $NaMoO_4.2H_2O$ | 0.00025 |
| $KH_2PO_4$ | 0.170 | $CuSo_4.5H_2O$ | 0.000025 |
| KI | 0.00083 | $CoCl_2.6H_2O$ | 0.000025 |
| Sequestrene 330-Fe | 0.040 | nicotinic acid | 0.001 |
| inositol | 0.100 | thiamine | 0.010 |
| piridoxine | 0.001 | sucrose | 30.0 |
| indole acetic acid | 0.000175 | agar | 8.0 |
| 6-benzylamino purine | 0.001125 | | |

The pH of the second regeneration medium is adjusted to 5.8 with NaOH prior to the addition of agar and autoclaving. The autoclaved medium is cooled to 50°

C., and the filter-sterilized plant growth regulators, indole acetic acid and 6-benzylamino purine, are added.

Finally, normal shoots are individually removed from the second regeneration medium and are placed on a third regeneration medium to accomplish root formation. Rooting usually occurs within two weeks. If not, shoots must be removed and subcultured every two weeks on the same medium. The third regeneration medium contains the following in water expressed in grams per liter:

| | | | |
|---|---|---|---|
| KNO$_3$ | 2.5 | Na$_2$MoO$_4$.2H$_2$O | 0.00025 |
| CaCl$_2$.2H$_2$O | 0.150 | CuSO$_4$.5H$_2$O | 0.000025 |
| MgSO$_4$.7H$_2$O | 0.250 | CoCl$_2$.6H$_2$O | 0.000025 |
| (NH$_4$)$_2$SO$_4$ | 0.134 | Sequestrene 330-Fe | 0.040 |
| NaH$_2$PO$_4$.H$_2$O | 0.150 | inositol | 0.100 |
| H$_3$BO$_3$ | 0.003 | piridoxine | 0.001 |
| ZnSO$_4$.7H$_2$O | 0.002 | nicotinic acid | 0.001 |
| MnSO$_4$.H$_2$O | 0.010 | thiamine | 0.010 |
| KI | 0.00075 | sucrose | 20.0 |
| agar | 8.0 | | |

The pH of the third regeneration medium is adjusted to 5.8 with NaOH prior to the addition of agar and autoclaving.

The resulting rooted F$_1$ hybrid plantlets are hardened for two weeks in a growth chamber in No. 16 silica sand in plastic trays covered with a clear plastic cover. Light is provided to the growth chamber at 200 $\mu$mol m$^{-2}$ s$^{-1}$ for 16 hours per day. The temperature in the growth chamber is provided at approximately 21° C. during the day and at approximately 18° C. during the night. Next, the hardened plants are transplanted into a mix composed of equal parts of peat, loam, and perlite present in 15 cm. plastic pots placed in a greenhouse where the temperature is maintained at approximately 18° to 25° C.

The resulting hand-emasculated F$_1$ interspecific hybrid plants next are backcrossed with pollen from *Brassica oleracea* using the same embryo culture protocol for a sufficient number of generations to yield a fully male and female fertile offspring which exhibits the 18 chromosome complement of *Brassica oleracea* together with cytoplasmic triazine tolerance which was derived from *B. napus*.

Such triazine tolerance commonly is exhibited when herbicides of this class are applied as a foliar spray at a rate in the range of approximately 0.28 to 1.5 kilograms per hectare. The rate of herbicide application may vary with the specific triazine herbicide selected as discussed hereafter. Preferably, the triazine herbicide is applied at the minimum rate necessary to destroy broadleaf weeds. The triazine tolerant plants possess the ability to withstand or to endure the herbicide while carrying on the usual plant functions in spite of the presence of the triazine in a concentration which would normally destroy a *Brassica oleracea* cole crop.

The triazine tolerance once present in *Brassica oleracea* can be introgressed into an open-pollinated cultivar of any *B. oleracea* cole crop by hybridization and repeated back-crossing into the commercial variety using the tolerant parent and progeny exclusively as the female parent. Because of the cytoplasmic nature of the triazine tolerance, this trait can only be maintained by collecting seed from the maternal parent. A totally new open-pollinated cultivar can be developed by crossing the triazine tolerant *Brassica oleracea* germplasm with pollen from a susceptible cole crop germplasm adapted to a specific area, selecting the fraction of the population with desirable agronomic traits and evaluating the lines in replicated trials. Also, a triazine tolerant F$_1$ hybrid cole crop cultivar can be developed by incorporating the triazine tolerance into an inbred line via sexual hybridization and introgression, and then producing the desired hybrid by the controlled pollination of this line with pollen from a susceptible inbred line which produces cole plants with desirable agronomic characteristics. As previously discussed, seed may only be collected from the triazine tolerant parent.

In accordance with the concept of the present invention a cole crop is produced in the substantial absence of unwanted broadleaf weeds while growing in a planting area which normally would have the propensity to form broadleaf weeds. *Brassica oleracea* plants are grown in the planting area which are fully male and female fertile, possess 18 chromosomes, and exhibit cytoplasmic triazine tolerance. Standard cole crop horticultural practices can be utilized during the planting of the cole crop. Such plants can be grown from seeds or from small plants which are transplanted into the planting area. The planting area is contacted with triazine in an amount sufficient to substantially destroy broadleaf weeds while maintaining the *Brassica oleracea* plants substantially intact. Next, the cole crop is harvested at the appropriate time in the plant's life cycle (e.g., at the bud stage in broccoli) using conventional hand or mechanized technology.

In a preferred embodiment of the process the triazine selected is a chloro-S-triazine. Representative chloro-S-triazines are atrazine, cyanazine, propazine, simazine, etc. The preferred chloro-S-triazines for use in the process of the present invention are atrazine (i.e., 2-chloro-4-ethylamino-6-isoproplamino-s-triazine) and cyanazine (i.e., [[4-chloro-6-(ethylamino)-s-triazine-2-yl]amino]-2-methylpriionitrile). Methoxy-S-triazines such as atratone, promatone, etc. may be utilized. Methylthio-S-triazines such as ametryn, prometryn, terbutryn, etc. may be utilized. Alternatively, a methylthio-A-Striazine such as metribuzin (i.e., 4-amino-6-tert-butyl-3-(methylthio)-as-triazine-5(OH)-one) may be utilized. It should be understood that the level of herbicide tolerance exhibited by the *Brassica oleracea* plants of the present invention may vary from one class of triazine herbicide to another. For instance, such plants commonly are more resistant to a chloro-S-triazine, such as atrazine, than a methylthio-AS-triazine, such as metribuzin. Such variations in herbicide tolerance will influence the optimum rate of herbicide application which can be determined by routine experimentation.

When carrying out the process of the present invention, the triazine may be applied to the planting area using a variety of techniques. For instance, the triazine may be applied to the soil of the planting area prior to the germination of the seeds which form the *Brassica oleracea* plants. A representative rate of application of atrazine to the soil is approximately 1.0 to 1.5 kilograms per hectare, and a representative rate of application of metribuzin to the soil is approximately 0.28 to 0.42 kilograms per hectare. In preferred embodiment the triazine is applied as a foliar spray to the planting area which includes the cole plants at a rate in the range of about 0.28 to 1.5 kilograms per hectare. Broadleaf weeds present in the planting area are substantially destroyed. Following the application of the triazine a substantially uniform population of the triazine tolerant *Brassica oleracea* plants remains in a substantially intact form. A pre-emergence triazine application will kill germinating broadleaf weeds; however, if subsequent cultivations are used or additional weed seeds are blown into the planting area, one or more repeat applications of the triazine herbicide may be required.

The present invention makes possible more efficient control of broadleaf weeds in a cole crop by permitting the use of a family of herbicides which heretofore could not be used. The herbicide utilized is well-known, is readily available, and has already undergone significant testing. Most triazines have a relatively low biological toxicity to mammals. Accordingly, no extensive herbicide pre-introduction trials should be required. The cole crop grower now is provided with a more efficient means to produce a crop while greatly minimizing the need for hand and mechanized cultivation to eliminate weeds and the concomitant expense associated therewith. Also, the ability for a grower to form a cole crop directly from seeds is rendered more feasible.

The following Examples are presented as specific illustrations of the claimed invention. The triazine-susceptible *Brassica oleracea* cultivars identified hereafter are commercially available. It should be understood, however, that the invention is not limited to the specific details set forth in the Examples.

EXAMPLE I

Seeds capable of forming the triazine tolerant spring canola cultivar 'OAC Triton' of *Brassica napus* subspecies *oleifera* are obtained from Beers Seeds Ltd., R.R.4, Arthur, Ontario, Canada NOG IAO. This cultivar possesses the same triazine tolerant cytoplasm as the less readily available spring canola breeding lines 84-01 and 84-03 which were employed in our early research efforts, and the usual complement of 38 chromosomes. As previously indicated, canola 'ATR-5TW' likewise could be employed.

Plants of the triazine tolerant canola are grown in a growth room illuminated with Sylvania metal arc lamps (215$\mu$mol m$^{-2}$5$^{-1}$ at canopy level) for 16 hours per day. The temperature in the growth room is maintained at 20° C. during the day and 16° C. during the night. These triazine tolerant plants are hand-emasculated and are pollinated in the bud stage with pollen from the 'Spartan Early' broccoli cultivar of *Brassica oleracea* subspecies *italica* which possesses the usual complement of 18 chromosomes. The 'Spartan Early' broccoli cultivar is totally lacking in triazine tolerance.

Twelve to seventeen days following pollination, as previously described, siliques are removed from the *Brassica napus* maternal parent, are surface sterilized and rinsed, intact ovules are obtained from the same, the ovules are placed in a petri dish, the ovules are split in half, the liquid in vitro culture medium of Monnier is added to the petri dish, the petri dish is sealed with parafilm, and the sealed petri dish is placed on a rotary shaker while present in a growth room.

After 14 to 21 days the surviving interspecific embryos are subjected to the regeneration media of Keller as previously described wherein $F_1$ hybrid plantlets are formed. The plantlets are hardened, transplanted, and grown in a greenhouse as previously described. It is found that the resulting $F_1$ hybrid is of reduced fertility, exhibits triazine tolerance, and possesses 37 chromosomes. However, it should be recognized that in many instances the $F_1$ hybrid will possess 28 chromosomes rather than 37 chromosomes.

The resulting $F_1$ hybrid is hand-emasculated and is pollinated in a first backcross with pollen from the 'Cleopatra' broccoli cultivar of *Brassica oleracea* subspecies *italica* which possesses the usual complement of 18 chromosomes. This change of pollen parent from the 'Spartan Early' broccoli cultivar to the 'Cleopatra' broccoli cultivar is not essential to the operation of desired genetic transfer but is done to assure that self-incompatibility is not a significant causation for the reduced fertility in the offspring. The same embryo culture and regeneration techniques are used. It is found that the resulting $BC_1$ plants continue to be of reduced fertility, exhibit triazine tolerance, and possess 26 chromosomes.

The resulting $BC_1$ plants are hand-emasculated and are pollinated in a second backcross with pollen from the 'Spartan Early' broccoli cultivar. The same embryo culture and regeneration techniques are used. It is found that the resulting $BC_2$ plants continue to be of reduced fertility, exhibit triazine tolerance, and possess 19 or 20 chromosomes.

The resulting $BC_2$ plants are hand-emasculated and pollinated in a third backcross with pollen from the 'Spartan Early' broccoli cultivar. Seeds form normally on the maternal parent. The $BC_3$ plants grown from these seeds possess 18, 19, or 20 chromosomes. Those $BC_3$ plants which possess the usual 18 chromosome complement of *Brassica oleracea* are fully male and female fertile and are the subject matter of the present invention. Such $BC_3$ plants possess triazine tolerance when atrazine is applied as a foliar spray at a rate of 1.5 kilograms per hectare. From these plants one may harvest a substantially uniform assemblage of seeds capable of forming male and female fertile *Brassica oleracea* plants possessing 18 chromosomes which exhibit the same triazine tolerance. A substantially uniform population of such plants can be formed from these seeds.

EXAMPLE II

The $BC_3$ *Brassica oleracea* broccoli plants formed in Example I can be used as a female parent of transfer triazine tolerance to *Brassica oleracea* cabbage plants of the subspecies *capitata* on an intraspecific basis. More specifically, such $BC_3$ plants can be pollinated with pollen from the 'Early Greenball' cultivar of cabbage, followed by backcrossing using the 'Early Greenball' cultivar as the recurrent pollen parent for a sufficient number of generations for the offspring to well exhibit cabbage characteristics while retaining the desired triazine tolerance.

EXAMPLE III

The $BC_3$ Brassica oleracea broccoli plants formed in Example I can be used as a female parent to transfer triazine tolerance to *Brassica oleracea* Savoy cabbage plants of the subspecies *sabauda* on an intraspecific basis. More specifically, such $BC_3$ plants can be pollinated with pollen from the 'Ice Queen' cultivar of Savoy cabbage, followed by backcrossing using the 'Ice Queen' cultivar as the recurrent pollen parent for a sufficient number of generations for the offspring to well exhibit Savoy cabbage characteristics while retaining the desired triazine tolerance.

EXAMPLE IV

The $BC_3$ *Brassica oleracea* broccoli plants formed in Example I can be used as a female parent to transfer triazine tolerance to *Brassica oleracea* cauliflower plants of the subspecies *botrytis* on an intraspecific basis. More specifically, such BC$_3$ plants can be pollinated with pollen from the 'Stokes Early Abundance' cultivar of cauliflower, followed by backcrossing using the 'Stokes Early Abundance' cultivar as the recurrent pollen parent for a suficient number of generations for the offspring to well exhibit cauliflower characteristics while retaining the desired triazine tolerance.

EXAMPLE V

The BC$_3$ *Brassica oleracea* broccoli plants forxed in Example I can be used as a female parent to transfer triazine tolerance to *Brassica oleracea* curly kale plants of the subspecies *fimbriata* on an intraspecific basis. More specifically, such BC$_3$ plants can be pollinated with pollen from the 'Green Curled Scotch' cultivar of curly kale, followed by backcrossing using the 'Green Curled Scotch' cultivar as the recurrent pollen parent for a sufficient number of generations for the offspring to well exhibit curly kale characteristics while retaining the desired triazine tolerance.

EXAMPLE VI

The BC$_3$ *Brassica oleracea* broccoli plants formed in Example I can be used as a female parent to transfer triazine tolerance to *Brassica oleracea* collard plants of the subspecies *acephala* on an intraspecific basis. More specifically, such BC$_3$ plants can be pollinated with pollen from the 'Vates' cultivar of collard followed by backcrossing using the 'Vates' cultivar as the recurrent pollen parent for a sufficient number of generations for the offspring to well exhibit collard characteristics while retaining the desired triazine tolerance.

EXAMPLE VII

The BC$_3$ *Brassica oleracea* broccoli plants formed in Example I can be used as a female parent to transfer triazine tolerance to *Brassica oleracea* kohl-rabi plants of the subspecies *gongyloides* on an intraspecific basis. More specifically, such BC$_3$ plants can be pollinated with pollen from the 'Early White Vienna' cultivar of kohl-rabi, followed by backcrossing using the 'Early White Vienna' cultivar as the recurrent pollen parent for a sufficient number of generations for the offspring to well exhibit kohl-rabi characteristics while retaining the desired triazine tolerance.

EXAMPLE VIII

The BC$_3$ *Brassica oleracea* broccoli plants formed in Example I can be used as a female parent to transfer triazine tolerance to *Brassica oleracea* Brussels sprouts plants of the subspecies *gemmifera* on an intraspecific basis. More specifically, such BC$_3$ plants can be pollinated with pollen from the 'Long Island Improved' cultivar of Brussels sprouts, followed by backcrossing using the 'Long Island Improved' cultivar as the recurrent pollen parent for a sufficient number of generations for the offspring to well exhibit Brussels sprouts characteristics while retaining the desired triazine tolerance.

EXAMPLE IX

The BC$_3$ *Brassica oleracea* broccoli plants formed in Example I can be used as a female parent to transfer triazine tolerance to *Brassica oleracea* Chinese kale plants of the subspecies *alboglabra* on an intraspecific basis. More specifically, such BC$_3$ plants can be pollinated with pollen from the 'Chinese Broccoli' cultivar of Chinese kale, followed by back-crossing using the 'Chinese Broccoli' cultivar as the recurrent pollen parent for a sufficient number of generations for the offspring to well exhibit Chinese kale characteristics while retaining the desired triazine tolerance.

It is to be understood that the foregoing detailed descriptions are given merely by way of illustration and that many variations may be made therein without departing from the concept of the invention as defined in the following claims.

We claim:

1. An improved process for producing a cole crop in the substantial absence of unwanted broadleaf weeds while growing in a planting area which normally would have the propensity to form such broadleaf weeds comprising:
    (a) growing *Brassica oleracea* plants in said planting area which are fully male and female fertile, possess 18 chromosomes, and exhibit cytoplasmic triazine tolerance,
    (b) contacting said planting area with triazine in an amount sufficient to substantially destroy broadleaf weeds while maintaining said *Brassica oleracea* plants substantially intact, and
    (c) harvesting the cole crop.

2. An improved process for producing a cole crop in the substantial absence of unwanted broadleaf weeds according to claim 1 wherein said *Brassica oleracea* plants are cabbage plants of the subspecies *capitata*.

3. An improved process for producing a cole crop in the substantial absence of unwanted broadleaf weeds according to claim 1 wherein said *Brassica oleracea* plants are Savoy cabbage plants of the subspecies *sabauda*.

4. An improved process for producing a cole crop in the substantial absence of unwanted broadleaf weeds according to claim 1 wherein said *Brassica oleracea* plants are cauliflower plants of the subspecies *botrytis*.

5. An improved process for producing a cole crop in the substantial absence of unwanted broadleaf weeds according to claim 1 wherein said *Brassica oleracea* plants are broccoli plants of the subspecies *italica*.

6. An improved process for producing a cole crop in the substantial absence of unwanted broadleaf weeds according to claim 1 wherein said *Brassica oleracea* plants are curly kale plants of the subspecies *fimbriata*.

7. An improved process for producing a cole crop in the substantial absence of unwanted broadleaf weeds according to claim 1 wherein said *Brassica oleracea* plants are collard plants of the subspecies *acephala*.

8. An improved process for producing a cole crop in the substantial absence of unwanted broadleaf weeds according to claim 1 wherein said *Brassica oleracea* plants are kohl-rabi plants of the subspecies *gonguloides*.

9. An improved process for producing a cole crop in the substantial absence of unwanted broadleaf weeds according to claim 1 wherein said *Brassica oleracea* plants are Brussels sprouts plants of the subspecies *gemmifera*.

10. An improved process for producing a cole crop in the substantial absence of unwanted broadleaf weeds according to claim 1 wherein said *Brassica oleracea* plants are Chinese kale plants of the subspecies *alboglabra*.

11. An improved process for producing a cole crop in the substantial absence of unwanted broadleaf weeds according to claim 1 wherein said triazine is atrazine.

12. An improved process for producing a cole crop in the substantial absence of unwanted broadleaf weeds according to claim 1 wherein said triazine is applied to the soil of said planting area in step (b) prior to the germination of the seeds which form said *Brassica oleracea* plants.

13. An improved process for producing a cole crop in the substantial absence of unwanted broadleaf weeds according to claim 1 wherein said triazine is applied to the plants growing in said planting area in step (b) as a foliar spray.

14. An improved process for producing a cole crop in the substantial absence of unwanted broadleaf weeds according to claim 1 wherein said triazine is applied to the plants growing in said planting area in step (b) as a foliar spray at a rate in the range of approximately 0.28 to 1.5 kilograms per hectare.

15. *Brassica oleracea* seeds which upon growth yield fully male and female fertile plants possessing 18 B chromosomes which exhibit cytoplasmic triazine tolerance when atrazine is applied as a foliar spray at a rate of 1.5 kilograms per hectare.

16. *Brassica oleracea* seeds according to claim 15 which yield cabbage plants of the subspecies *capitata*.

17. *Brassica oleracea* seeds according to claim 15 which yield Savoy cabbage plants of the subspecies *sabauda*.

18. *Brassica oleracea* seeds according to claim 15 which yield cauliflower plants of the subspecies *botrytis*.

19. *Brassica oleracea* seeds according to claim 15 which yield broccoli plants of the subspecies *italica*.

20. *Brassica oleracea* seeds according to claim 15 which yield curly kale plants of the subspecies *fimbriata*.

21. *Brassica oleracea* seeds according to claim 15 which yield collard plants of the subspecies *acephala*.

22. *Brassica oleracea* seeds according to claim 15 which yield kohl-rabi plants of the subspecies *gongyloides*.

23. *Brassica oleracea* seeds according to claim 15 which yield Brussels sprouts plants of the subspecies *gemmifera*.

24. *Brassica oleracea* seeds according to claim 15 which yield Chinese kale plants of the subspecies *alboglabra*.

25. *Brassica oleracea* seeds according to claim 15 which are provided as a substantially uniform assemblage.

26. *Brassica oleracea* plants which are fully male and female fertile, possess 18 chromosomes, and exhibit cytoplasmic triazine tolerance when atrazine is applied as a foliar spray at a rate of 1.5 kilograms per hectare.

27. *Brassica oleracea* plants according to claim 26 which are cabbage plants of the subspecies *capitata*.

28. *Brassica oleracea* plants according to claim 26 which are Savoy cabbage plants of the subspecies *sabauda*.

29. *Brassica oleracea* plants according to claim 26 which are cauliflower plants of the subspecies *botrytis*.

30. *Brassica olercacea* plants according to claim 26 which are broccoli plants of the subspecies *italica*.

31. *Brassica oleracea* plants according to claim 26 which are curly kale plants of the subspecies *fimbriata*.

32. *Brassica oleracea* plants according to claim 26 which are collard plants of the subspecies *acephala*.

33. *Brassica oleracea* plants according to claim 26 which are kohl-rabi plants of the subspecies *gongyloides*.

34. *Brassica oleracea* plants according to claim 26 which are Brussels sprouts plants of the subspecies *gemmifera*.

35. *Brassica oleracea* plants according to claim 26 which are Chinese kale plants of the subspecies *alboglabra*.

36. *Brassica oleracea* plants according to claim 26 which are provided as a substantially uniform population.

* * * * *